US009663531B2

(12) United States Patent  
Dufour et al.

(10) Patent No.: US 9,663,531 B2
(45) Date of Patent: May 30, 2017

(54) PROCESS FOR THE INDUSTRIAL SYNTHESIS OF SORDIDIN

(71) Applicants: M2I DEVELOPMENT, Lacq (FR); M2I SALIN, Saint Cloud (FR)

(72) Inventors: Samuel Dufour, Orthez (FR); Valérie LeJeune, Bouillargues (FR); Hubert Sevestre, Mourenx (FR)

(73) Assignees: M2I DEVELOPMENT, Lacq (FR); M2I SALIN, Saint Cloud (FR)

( * ) Notice: Subject to any disclaimer, the term of this patent is extended or adjusted under 35 U.S.C. 154(b) by 0 days.

(21) Appl. No.: 15/109,053

(22) PCT Filed: Dec. 30, 2014

(86) PCT No.: PCT/EP2014/079470
§ 371 (c)(1),
(2) Date: Aug. 19, 2016

(87) PCT Pub. No.: WO2015/101636
PCT Pub. Date: Jul. 9, 2015

(65) Prior Publication Data
US 2016/0355526 A1 Dec. 8, 2016

(30) Foreign Application Priority Data
Dec. 30, 2013 (FR) ..................... 13 63699

(51) Int. Cl.
C07D 317/00 (2006.01)
C07D 493/08 (2006.01)
C07D 317/26 (2006.01)

(52) U.S. Cl.
CPC ......... *C07D 493/08* (2013.01); *C07D 317/26* (2013.01)

(58) Field of Classification Search
CPC ........................... C07D 493/08; C07D 317/26
USPC ........................................................ 549/454
See application file for complete search history.

(56) References Cited

PUBLICATIONS

Jayaraman et al, Synthesis, Analysis, and Field Activity of Sordidin, A Male-produced Aggregation Pheromone of the Banana Weevil, Cosmopolites sordidus, Journal of Chemical Ecology, vol. 23, No. 4, 1997, pp. 1145-1161.*

Beauhaire et al., "Identification and Synthesis of Sordidin, a Male Pheromone Emitted by Cosmopolites sordidus," Tetrahedron Letters, vol. 36, No. 7, 1995 pp. 1043-1046.
Ducrot, "Efficient Synthesis of Sordidin, A Male Pheromone Compound Emitted by Cosmopolites Sordidus," Synthetic Communications, vol. 26, No. 21, 1996 (published online Aug. 23, 2006), pp. 3923-3928 (8 pages total).
Enders et al., "First Asymmetric Synthesis of (+)-Sordidin and (−)-7-epi-Sordidin, Aggregation Pheromones of the Banana Weevil Cosmopolites sordidus," European Journal of Organic Chemistry, 2005, pp. 2677-2683.
French Preliminary Search Report, dated Oct. 14, 2014, for French Application No. 1363699.
International Search Report (Forms PCT/ISA/220 and PCT/ISA/210), dated Mar. 3, 2015, for International Application No. PCT/EP2014/079470.
Lanners et al., "A Convergent Strategy for the Pamamycin Macrodiolides: Total Synthesis of Pamamycin-607, Pamamycin-593, and Pamamycin-621D Precursors," Angewandte Chemie International Edition, vol. 46, 2007, pp. 7086-7089.
Mori et al., "Synthesis and Absolute Configuration of Sordidin, the Male-Produced Aggregation Pheromone of the Banana Weevil, Cosmopolites sordidus," Tetrahedron Letters, vol. 37, No. 21, 1996, pp. 3741-3744.
Mori, "Molecular Asymmetry and Pheromone Science," Bioscience, Biotechnology, and Biochemistry, vol. 60, No. 12, 1996, pp. 1925-1932.
Ndiege et al., "Convenient Synthesis and Field Activity of a Male-Produced Aggregation Pheromone of Cosmopolites sordidus," Naturwissenschaften, vol. 83, 1996, pp. 280-282.
Wardrop et al., "Synthesis of (±)-7-episordidin," Tetrahedron Letters, vol. 43, 2002, pp. 737-739.
Yadav et al., "Stereoselective synthesis of (+)-sordidin, the male-produced aggregation pheromone of the banana weevil Cosmopolites sordidus," Tetrahedron, vol. 64, 2008 (available online Dec. 24, 2007), pp. 2063-2070.
Yamada et al., "New Synthetic Intermediate for Trans-8-Methylhydrindanones," Tetrahedron Letters, vol. 31, No. 17, 1990, pp. 2407-2410.

* cited by examiner

*Primary Examiner* — T. Victor Oh
(74) *Attorney, Agent, or Firm* — Birch, Stewart, Kolasch & Birch, LLP

(57) ABSTRACT

The present invention relates to a process for preparing sordidin, comprising a step of preparing 4-(2-ethyl-1,3-dioxolan-2-yl)pentan-2-one by means of a reaction in which 2-ethyl-2-(pent-4-en-2-yl)-1,3-dioxolane is oxidized in the presence of a catalyst chosen from the group comprising organometallic complexes of transition metals.

18 Claims, No Drawings

PROCESS FOR THE INDUSTRIAL SYNTHESIS OF SORDIDIN

This invention relates to a process for obtaining sordidin comprising a process for preparing a reaction intermediate for the purposes of industrially synthesising sordidin, aggregation pheromone emitted by the black male banana weevil (*Cosmopolites sordidus*).

The "*Cosmopolites sordidus*" weevil is the most devastating insect for banana plantations and it has spread throughout the entire world. Synthetic sordidin is used in pit fall traps (associated with an insecticide or with a pathogen) placed on the ground in banana plantations, in order to reduce and control weevil populations. Given the volumes likely to be used in treating the banana plantations, it is important to be able to industrially synthesise this pheromone compound using abundant and/or inexpensive raw materials and at least cost. This invention has for object a new process for the industrial synthesis of a key intermediate of sordidin.

Sordidin with chemical formula 2,8-dioxa 1-ethyl 3,5,7-trimethyl bicyclo(3,2,1) octane has in its chemical structure four chiral centres in positions 1,3,5 and 7. Due to its bicyclic structure (cf. diagram 1), there are four isomers a, b, c and d which are differentiated by the absolute configuration of the carbons in positions 3 and 7, with the configuration of the centres 1 and 5 being frozen.

The isomer d (1S,3R,5R,7S) corresponds to the natural pheromone of "*Cosmopolites sordidus*", it was isolated and its structure characterised for the first time in 1995 (J. Beauhaire, Tetrahedron Letters, 36 (7) 1043-1046, 1995) (cf. diagram 1)

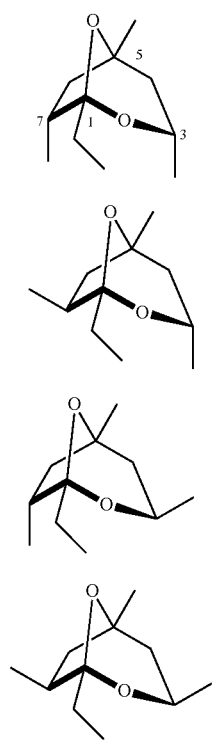

a b c d

Diagram 1: Chemical Formula of Isomers a, b, c, d of Sordidin

The asymmetry of the molecules is important from a chemical as well as biological standpoint (K. Mori, Biosci. Biotech. Biochem., 60 (12) 1925-1932, 1996). For example, for certain insects, a single stereo-isomer can be bioactive and the others can inhibit the action of the pheromone. In the scents given off by the banana weevil, sordidin is found only in the form of stereo-isomer d alone (1S,3R,5R,7S) (K. Mori, Tetrahedron Lett., 37 3741-3744, 1996), however studies in the field have shown that the racemic mixture of the stereo-isomers remains bioactive (I. O. Ndiege, Naturwissenschaften, 83 280-282 1996). Consequently, in the case of sordidin, the processes for synthesising leading to pure enantiomers (D. J. Wardrop, Tetrahedron Lett., 43 737-739, 2002; D. Enders, Eur. J. Org. Chem., 2677-2683 2005, and J. S. Yadav, Tetrahedron, 64 2063-2070, 2008) are not the most interesting because implementing them is complex and makes use of expensive catalysts, for a limited application gain.

A process for racemic synthesising was described by Ducrot (P. H. Ducrot, Synth. Comm., 26 (21) 3923-3928, 1996). This synthesis has for starting point an inexpensive raw material: 3-pentanone (noted as 1 in the diagram 2), contrary to the synthesis proposed by Jayaraman (S. Jayaraman, J. Chem. Ecol., 23 1145-1161, 1997) which uses a raw material that is not very accessible industrially.

The process for synthesising according to Ducrot comprises twelve steps. The applicant intends by the word step any chemical reaction and its treatment resulting in the isolation of an intermediate.

During the Ducrot process, using 3-pentanone and after 2 reaction steps, the following olefin intermediate is synthesised: 2-ethyl-2-(pent-4-en-2-yl)-1,3-dioxolane (compound 3 hereinbelow).

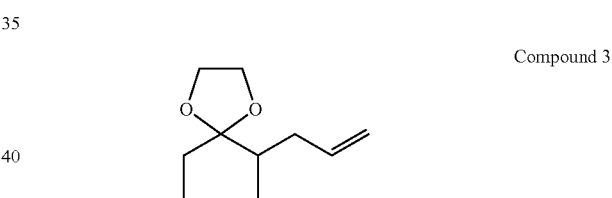

Compound 3

According to the process described by Ducrot, this compound 3 is then transformed via 6 other steps into the corresponding ketone (compound 4 hereinbelow): 4-(2-ethyl-1,3-dioxolan-2-yl)pentan-2-one.

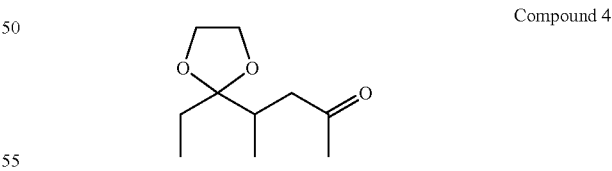

Compound 4

The compound 4 is in turn transformed into sordidin following 4 reaction steps such as described by Ducrot.

Note that the six steps of transforming the compound 3 into 4 result not only in a drop in global output of the synthesis but they also use reagents that are not recommended on an industrial scale including in particular osmium tetroxide ($OsO_4$) which is very toxic.

It thus appears that there is a need for a process for synthesising sordidin that only involves a number that is as reduced as possible of reaction steps making it possible to obtain sordidin with industrially optimum outputs and also by avoiding as much as possible the use of reagents and/or solvents that are expensive, dangerous or extremely harmful.

This invention therefore proposes to provide a new process for synthesising sordidin involving a reduced number of reaction steps, said process comprising a new synthesis route of an intermediate.

To this effect, this invention as such relates to a process for preparing sordidin comprising a step for preparing 4-(2-ethyl-1,3-dioxolan-2-yl)pentan-2-one (compound 4)

compound 4

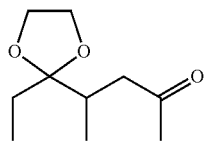

by means of a reaction in which 2-ethyl-2-(pent-4-en-2-yl)-1,3-dioxolane (compound 3)

compound 3

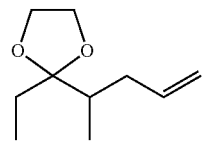

is oxidised in the presence of a catalyst chosen from the group comprising organometallic complexes of transition metals.

In a particular embodiment, the process according to this invention comprises the transforming of the compound 4 into compound 5 by magnesium coupling with alkyl magnesium halide, then the transforming of the compound 5 into compound 6 by oxidation, for example with a peracide such as peracetic acid, perpropionic acid or meta-chloroperoxybenzoic acid, then transforming the compound 6 into compound 7 by an opening of the epoxide, for example with a metal hydride, and conversion of the compound 7 into sordidin par cyclisation, for example in an acid medium.

This invention as such makes it possible to obtain sordidin via a process wherein the compound 4 is obtained in a single step using compound 3.

This process makes it possible as such to substantially reduce the number of steps during the synthesising of sordidin in relation to a process such as described by Ducrot.

Indeed, in the process disclosed by Ducrot, the converting of the compound 3 into compound 4 involves no less than six steps while the process according to this invention makes it possible to pass from compound 3 to compound 4 in a single step. As such the global output of the synthesis of sordidin according to the invention, comprising the process for obtaining compound 4 by means of a reaction in which compound 3 is oxidised in the presence of a catalyst chosen from the group comprising organometallic complexes of transition metals, is substantially increased.

In addition, the solvents implemented, alone or as a mixture, in the step of converting the compound 3 into 4, such as water, acetone or DMF for example, are substantially less dangerous and better adapted to industrial development than the solvents described by Ducrot (THF and CH2Cl2).

The process according to this invention therefore has the precious advantage of improving the output of the global reaction of the synthesis of sordidin using compound 3 while also implementing solvents that are hardly harmful or not harmful at all with regards to operators as well as the environment. Finally, such a process according to the invention can be industrialised easily.

Diagram 2 hereinbelow summarises the process for obtaining sordidin comprising the process for obtaining compound 4 using compound 3, according to this invention.

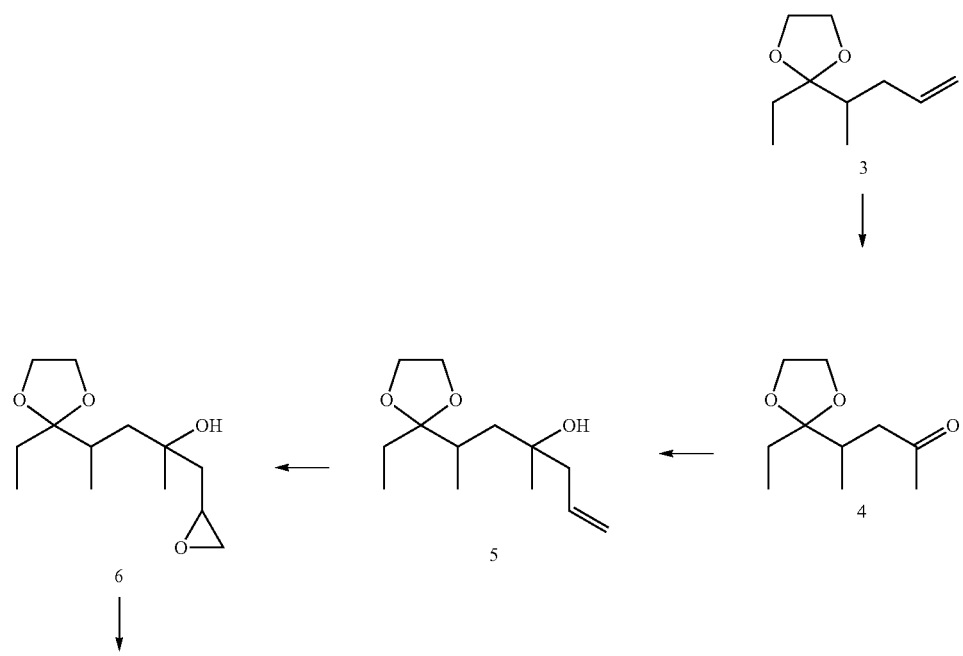

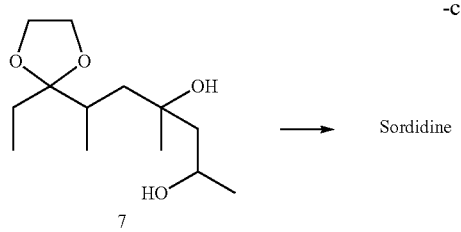

→ Sordidine

Drawing 2: Synthesis of sordidin in 5 steps according to the invention using compound 3.

The object of the invention is therefore a process for synthesising sordidin comprising a step that makes it possible to obtain compound 4 using compound 3 via an oxidation reaction in the presence of a catalyst chosen from organometallic complexes of transition metals.

In an embodiment of the invention, the oxidation reaction of compound 3 into compound 4 is carried out in the presence of an oxidising agent chosen from air, oxygen-enriched air, oxygen $O_2$ and hydroperoxides of general formula R—OOH wherein R can be a hydrogen atom, a linear or branched $C_1$-$C_6$ alkyl group, particularly a terbutyl group or a cumyl aromatic group.

In this particular embodiment of the invention, the oxidising agent of the oxidation reaction of compound 3 into compound 4 can be chosen from air, oxygen, tBuOOH or $H_2O_2$.

In an embodiment of the invention the catalyst of the oxidation reaction of compound 3 into compound 4 is chosen from organometallic complexes of transition metals. In such a particular embodiment of the invention, the catalyst of the oxidation reaction of compound 3 into compound 4 can be complexed by a ligand chosen from amines, phosphines and phtalocyanines.

In a particular embodiment of the invention, the catalyst of the oxidation reaction of compound 3 into compound 4 is chosen from organometallic complexes of transition metals with a Ni, Rh, Ir, Pd, Co or Pt base.

In a particular embodiment the catalyst of the oxidation reaction of compound 3 into compound 4 can be chosen from Palladium (II) compounds such as $PdCl_2$, $Pd(Acetate)_2$, Pd(Acetate)(triflate), $Pd(OH)_2$ or $PdBr_2$. In a further preferred embodiment, the catalyst of the oxidation reaction of compound 3 into compound 4 is $Pd(Acetate)_2$.

In another particular embodiment of the invention, the catalyst of the oxidation reaction of compound 3 into compound 4 can be chosen from Nickel (II) compounds such as $Ni(Acetate)_2$, $NiCl_2$ or $NiBr_2$.

In an embodiment of the invention, the catalyst of the oxidation reaction of compound 3 into compound 4 can be chosen from the Cobalt compounds $Co(No_3)_2$, $CoCl_2$, $CoBr_2$ or $Co(Acetate)_2$.

Finally, in another embodiment of the invention, the catalyst of the oxidation reaction of compound 3 into compound 4 can be chosen from Rhodium (III) compounds such as Rh(Cl) or $Rh(ClO_4)_3$.

In an embodiment of the invention, the process according to the invention comprises the adding of a regenerator of the catalyst of the oxidation reaction of compound 3 into compound 4, which can be chosen from copper or iron-based regenerators such as CuCl, CuCl2, CuBr, CuBr2, CuAcetate, FeCl2, FeCl3.

In such an embodiment of the invention, the regenerator of the catalyst can be associated with one or several ligands chosen from les phtalocyanines.

In a particular embodiment of the invention, the oxidation reaction of the compound 3 into 4 is carried out in the presence of a solvent or of a mixture of solvents chosen from water, alcoholic solvents, acidic solvents, solvents of the ketone type, ether solvents, nitrogen solvents, as well as solvents of the liquid polymer type or mixtures thereof.

In a particular embodiment of the invention, the alcoholic solvent can be chosen from methanol (MeOH) or terbutyl alcohol (tert-BuOH).

In a more particular embodiment, the acidic solvent can be chosen from the aqueous solutions of hydrochloric acid (HCl) or of perchloric acid ($HClO_4$).

In another embodiment, the solvent of the ketone type can be chosen from acetone or methyl ethyl ketone.

In another embodiment, the solvent of the nitrogen type can be chosen from DMA (dimethylacetamide), dimethyl formamide (DMF) or NMP (N-methyl-2pyrrolidone).

In another embodiment, the solvent of the ether type can be chosen from DME (dimethoxyethane), diglyme, or MTBE (methyltertiobutylether).

In another embodiment, the solvent of the liquid polymer type can be chosen from glycol polyethylenes with an average molecular mass as a number less than 1000 or mixtures thereof.

In a particular embodiment of the invention the oxidation reaction of compound 3 into compound 4 is carried out in the presence of at least one solvent chosen from water, DMF, DMA, acetone, heptane, tert-BuOH or mixtures thereof The process according to this invention begins by obtaining the compound 3 according to the method described by Ducrot using chemical reagents that are easily available off the shelf.

The compound 3 is as such introduced, preferably under stirring, into an adequate reactor and are added the solvent or the solvent mixture, the catalyst and the possible regenerator of the catalyst, the oxidising agent as well as possibly the ligand of the catalyst or of the regenerator.

The reaction medium is then brought to a temperature which can be between the ambient temperature and a temperature of about 100° C., and this according to the nature of the solvent implemented.

In an embodiment of the invention, the oxidation of the compound 3 into 4 can be carried out at a temperature between about 20° C. and about 100° C., particularly between about 25° C. and about 80° C., more particularly between about 40° C. and about 80° C., more particularly still between about 50° C. and about 60° C.

The reaction medium can be mixed and stirred and the pressure inside the reactor can be increased in such a way as to conduct the reaction at a pressure between atmospheric pressure and a pressure of about 30 bars. In an embodiment of the invention, the oxidation of the compound 3 into 4 can be carried out at a pressure between atmospheric pressure and about 30 bars more particularly between about 1 bar and about 20 bars, more particularly still between about 1 bar and about 10 bars, more particularly still at around 5 bars.

After a certain reaction time which can be between 1 and 20 hours, the reaction is stopped by lowering the temperature and/or the pressure in the reaction chamber.

Typically, the forming of the compound 4 is followed by Gas Chromatography in order to evaluate the progress of the reaction. The compound 4 can be recovered by liquid-liquid extracting and/or decanting followed by an evaporating and by a possible distilling in order to obtain the compound 4 with an adequate degree of purity to pursue the synthesising and the obtaining of the sordidin.

The molar ratios of the catalyst with respect to compound 3 can be between 0.1% and 10%, more preferably between 0.1%, and 5% and more preferably still between 0.1% and 1%. The quantity of regenerator will be between 1 to 10 times that of the catalyst and that of a possible ligand will be of 1 molar equivalent in relation to the catalyst.

As such this invention aims for a process for preparing sordidin comprising a step of preparing compound 4 by means of an oxidation reaction of the compound 3 such as described hereinabove followed by the transforming of the compound 4 into compound 5 by magnesium coupling with alkyl magnesium halide, then the transforming of the compound 5 into compound 6 by oxidation, for example with a peracide such as peracetic acid, perpropionic acid or metachloroperoxybenzoic acid, then transforming of compound 6 into compound 7 by an opening of the epoxide, for example with a metal hydride, and conversion of the compound 7 into sordidin par cyclisation, particularly by cyclisation in an acid medium. The various steps that make it possible to obtain sordidin using compound 4 are described in detail by Ducrot in the following publication: P. H. Ducrot, Synth. Comm., 26 (21) 3923-3928, 1996.

This invention also relates to a process for preparing 4-(2-ethyl-1,3-dioxolan-2-yl)pentan-2-one (compound 4)

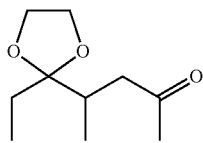

compound 4 by means of a reaction in which 2-ethyl-2-(pent-4-en-2-yl)-1,3-dioxolane (compound 3)

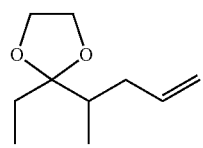

compound 3 is oxidised in the presence of a catalyst chosen from the group comprising organometallic complexes of transition metals.

As such, using 3-pentanone, by following the process according to this invention, sordidin can be obtained in 7 steps instead of the 12 steps taught by Ducrot. The reduction in the number of reaction steps and intermediates according to this process positively affects the global output of the reaction of the synthesis of sordidin and furthermore makes it possible to overcome the use of dangerous, expensive and/or toxic reagents such as osmium tetroxide.

Finally another object of the invention consists of a composition of sordidin that has a particular distribution of isomers of sordidin thanks to the process for preparing according to the invention.

As such this invention has for object a composition of sordidin characterised in that it comprises the 4 diastereoisomers a, b, c and d (such as indicated in diagram 1) of which the respective proportions measured by gas phase chromatography are comprised in the intervals: 31-36%; 16-20%; 16-20%; 28-32%.

In particular, a composition according to the invention is a composition of sordidin characterised in that the respective proportions of the four diastereoisomers a, b, c and d, measured by gas phase chromatography, are about 34%; 19%; 16.9% and 30.1%.

Such a composition can be obtained par a process according to this invention such as described in this description and which makes it possible to obtain as a majority quantity the isomers a and c.

The measurement of the proportions of the 4 diastereoisomers a, b, c and d is carried out by the measurement of the quantity of these isomers via the measurement of the area under the curve following a measurement by gas phase chromatography in conditions such as described in the Examples section, hereinafter. The respective percentages of the 4 diastereoisomers are expressed with respect to the total quantity of sordidin, with all isomers taken as a whole.

EXAMPLES

The starting product, compound 3: 2-ethyl-2-(pent-4-en-2-yl)-1,3-dioxolane can be obtained according to the Ducrot procedure, using 3-pentanone after two first steps described in: P. H. Ducrot, Synth. Comm., 26 (21) 3923-3928, 1996.

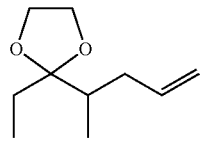

Compound 3

The other reagents are purchased from conventional chemical suppliers.

Analysis in Gas Phase Chromatography

The reaction follow-up of the various steps of the synthesis of sordidin is carried out by Gas Phase Chromatography (CPG). The results are expressed as a relative percentage. The relative quantities of compounds are evaluated via measuring the area under the curve. The analyses were carried out in the following conditions: CPG device of the Hewlett Packard brand (5890 Series II), provided with an FID detector (Flame Ionisation Detector) and with a HP5 column (Agilent J&W) 30 m×0.52 mm Film 0.88 µm, with a helium pressure from 3 to 10 psi, an injector temperature of 250° C., a detector temperature of 280° C. The following were also used: an initial oven temperature of 50° C., an initial time of 3 min a ramp 1 of 10° C./min, a final temperature 1 of 260° C. and a dwell time 1 of 5 min.

The samples to be analysed were prepared by diluting 100 mg of synthetic intermediate or of the product to analysed in acetonitrile (QSP 20 ml). The volume of sample injected into the CPG is 1 µl.

Example 1

Oxidation Reaction Under Air Pressure in the Conditions: Air Pressure (6 Bars), Catalyst PdCl2 Plus CuCl in a Water-DMF Mixture Into a 250 ml tricol flask provided with a stirring platform and with a two-blade stirrer are introduced successively 93.5 ml of DMF, 19.5 ml of water, 43 mg of palladium chloride, 295 mg of cuprous chloride and finally 8.5 g of compound 3.

The reaction medium is heated to 80° C. and compressed air is injected resulting in an increase in the pressure of the reactor to 5 bars with a slight renewal of air. After 8 h 30 of stirring, 13% conversion is observed by CPG and the relative purity of the compound 4 formed is 11%. The conversion rate obtained led the inventors to optimise the reaction conditions of which details are provided in the following examples.

Example 2

Oxidation Reaction Under Air Pressure in the Conditions: Air Pressure (6 Bars), Catalyst PdCl2 Plus CuCl in a Water-DMA Mixture In a 70 L reactor, are loaded under stirring, successively 44 kg dimethylacetamide (DMA), 2.6 kg of the compound 3, 6.6 kg of water, 13.8 g of palladium chloride, and 93 g of cuprous chloride. The reaction medium is heated to 80° C. and compressed air is injected resulting in an increase in the pressure of the reactor to 6 bars with a slight renewal of air. The forming of the compound 4 is followed by gas phase chromatography in the conditions described hereinabove.

After 12 h of stirring, it is observed that the starting product has disappeared. The reaction medium is cooled to ambient temperature then water is added (26 kg). Exothermicity is observed. The compound 4 is then recovered by decanting followed by four extracting with methyl-tert-butyl ether MTBE (5V) and completed by two washings with water of the organic phases (1V). After evaporation, the fractions are gathered together and distilled to 72° C. at 4 mbar. The fractions are redistilled, until the obtaining of a pale yellow colour liquid (2.2 kg of compound 4, output 80%, purity CPG=94%).

Example 3

Oxidation reaction under atmospheric air pressure, in the conditions: 60° C., catalyst palladium acetate in acetone, t-butylhydroperoxide oxidant Into a 250 ml tricol flask provided with a stirring platform and with a two-blade stirrer are introduced 100 ml of acetone, 65.6 ml of t-butyl hydroperoxide (tBuOOH) then under stirring 1.76 g of catalyst: palladium acetate and finally 27.93 g of compound 3.

The reaction medium is heated to 60° C. under atmospheric pressure. The forming of the compound 4 is followed by gas phase chromatography.

After 14 h of stirring (the conversion rate is 97.9%), the reaction medium is cooled to ambient temperature.

100 ml of a solution containing 50 g sodium thiosulfate and 100 ml of MTBE is then added. The reaction medium is filtered and after decanting the upper organic phase is recovered. After evaporation of the solvents at 60° C., followed by distilling in a vacuum at a pressure of 2 mbar, the compound 4, 11.1 g (36.3% of yield) is obtained in the form of a pale yellow limpid liquid with a relative purity of 90.7% by CPG.

Examples 4 to 8

Examples 4 to 8 make it possible to show the various operating conditions considered concerning the step of transforming the compound 3 into compound 4 in the framework of this invention.

The various processes tested are distributed into two major types, pressurised tests which follow the experimental protocol described in example 2, the atmospheric pressure tests which follow the protocol described in example 3.

|  | Ex 1 | Ex 2 | Ex 3 | Ex 4 | Ex 5 | Ex 6 | Ex 7 | Ex 8 |
|---|---|---|---|---|---|---|---|---|
| Type of condition | Ex 2 | Ex 2 | Ex 3 | Ex 2 | Ex 3 | Ex 3 | Ex 3 | Ex 3 |
| Oxidant | air | air | tBuOOH | Air enriched | tBuOOH | $H_2O_2$ | tBuOOH | tBuOOH |
| Catalyser (and possible regenerator) | $PdCl_2$ + CuCl | $PdCl_2$ + CuCl | ePdO (Acetate)$_2$ | $PdCl_2$ + CuCl | Pd (Acetate) (Triflate) | $PdOAC_2$ | $PdOAC_2$ | Pd $(OAc)_2$ + ligand NaOAC |
| Solvent | DMF + water | DMA + water | Acetone | Acetone | Acetone | Tert-BuOH | Acetone | Heptane |
| Temperature (° C.) | 80 | 80 | 60 | 80 | 50 | 50 | 60 | 98 |
| Pressure (atm) | 5 | 6 | 1 | 5 | 1 | 1 | 1 | 1 |
| Conversion rate of the compound 3 into 4 | 13% | 91% | 97% | 91% | 67% | 80% | 98% | >95% |

Example 9

Using compound 4, the compound 5 is obtained by reaction with magnesium allyl chloride, then the compound 6 by controlled oxidation and this latter compound is then obtained by acid hydrolysis. The sordidin obtained is characterised by gas phase chromatography. The distribution of the 4 diastereoisomers a, b, c and d of sordidin is measured such as indicated in diagram 1. The elute times correspond to the four diastereoisomers such as was shown by Beauhaire (Tetrahedron Letters, 36 (7) 1043-1046, 1995).

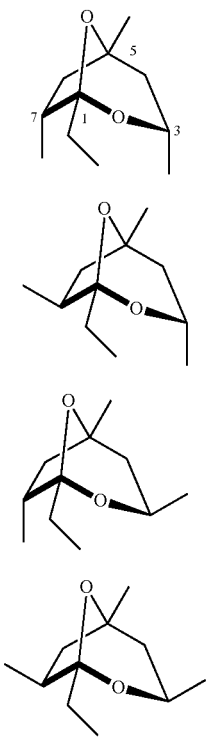

Diagram 1: Chemical Formula of Isomers a, b, c, d of Sordidin

The analysis of the quantity, by calculating the area under the curve, of the 4 diastereoisomers of sordidin contained in the sordidin mixture obtained gives the following distribution: a: 34%; b: 19%; c: 16.9%; d: 30.1%.

The invention claimed is:

1. A process for preparing sordidin comprising a step for preparing 4-(2-ethyl-1,3-dioxolan-2-yl)pentan-2-one (compound 4)

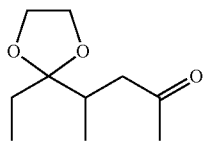

compound 4 by means of a reaction in which 2-ethyl-2-(pent-4-en-2-yl)-1,3-dioxolane (compound 3)

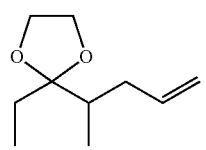

compound 3 is oxidised in the presence of a catalyst comprising an organometallic complex of a transition metal.

2. The process according to claim 1, wherein the oxidation reaction is carried out in the presence of an oxidising agent chosen from air, oxygen-enriched air, oxygen $O_2$ and hydroperoxides with the formula R—OOH wherein R can be a hydrogen atom, a linear or branched $C_1$-$C_6$ alkyl group.

3. The process according to claim 1, wherein the catalyst comprises a Ni, Rh, Ir, Pd, Co or Pt base.

4. The process according to claim 1, wherein the catalyst is chosen from Palladium (II) compounds from Nickel (II) compounds from the Cobalt compounds, or from Rhodium (III) compounds.

5. The process according to claim 1, wherein the catalyst is complexed by a ligand chosen from amines, phosphines and phtalocyanines.

6. The process according to claim 1, wherein a catalyst regenerator is added.

7. The process according to claim 6, wherein the catalyst regenerator is chosen from copper and iron-based regenerators.

8. The process according to claim 1, wherein the catalyst is Pd(Acetate)$_2$.

9. The process according to claim 1, wherein the oxidation reaction of compound 3 into compound 4 is carried out in the presence of at least one solvent chosen from water, alcoholic solvents, acidic solvents, ketone solvents, ether solvents, nitrogen solvents, as well as liquid polymer solvents.

10. The process according to claim 1, wherein the oxidation reaction of compound 3 into compound 4 is carried out in the presence of at least one solvent chosen from water, DMF, DMA, acetone, heptane, tertBuOH and mixtures thereof.

11. The process according to claim 1, wherein the oxidation reaction is carried out under a pressure between atmospheric pressure and 30 bars.

12. The process according to claim 1, wherein the oxidation reaction is carried out at a temperature between 25° C. and 100° C.

13. A process for synthesising sordidin wherein it comprises a process according to claim 1, followed by the modification of the 4-(2-ethyl-1,3-dioxolan-2-yl)pentan-2-one (compound 4)

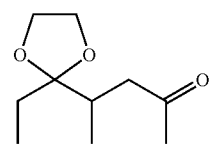

compound 4 by magnesium coupling with alkyl magnesium halide, oxidation, opening of the epoxide, and conversion into sordidin by cyclisation.

14. The process according to claim 2, wherein R is a terbutyl group or a cumyl aromatic group.

15. The process according to claim 4, wherein the Palladium (II) compound is selected from the group consisting of PdCl$_2$, Pd(Acetate)$_2$, Pd(Acetate)(triflate), Pd(OH)$_2$ and PdBr$_2$, the Nickel (II) compound is selected from the group consisting of Ni(Acetate)$_2$, NiCl$_2$ and NiBr$_2$, the Cobalt compound is selected from the group consisting of Co(No$_3$)$_2$, CoCl$_2$, CoBr$_2$ and Co(Acetate)$_2$, or the Rhodium (III) compound is selected from the group consisting of Rh(Cl) and Rh(ClO$_4$)$_3$.

16. The process according to claim 7, wherein the copper or iron-based regenerator is selected from the group consisting of CuCl, CuCl$_2$, CuBr, CuBr$_2$, CuAcetate, FeCl$_2$, and FeCl$_3$.

17. The process according to claim 11, wherein the oxidation reaction is carried out under a pressure between atmospheric pressure and 5 bars.

18. The process according to claim 12, wherein the oxidation reaction is carried out at a temperature between 40° C. and 80° C.

* * * * *